(12) United States Patent
Salvi et al.

(10) Patent No.: US 7,547,792 B2
(45) Date of Patent: Jun. 16, 2009

(54) PROCESS FOR PURIFYING THIOCTIC ACID IN WATER

(75) Inventors: Annibale Salvi, Milan (IT); Antonio Nardi, Paderno Dugnano (IT); Giacomo Bruno, Caravaggio (IT)

(73) Assignee: Laboratorio Chimico Internazionale S.p.A., Milan (IT)

( * ) Notice: Subject to any disclaimer, the term of this patent is extended or adjusted under 35 U.S.C. 154(b) by 0 days.

(21) Appl. No.: 11/909,305

(22) PCT Filed: Mar. 21, 2006

(86) PCT No.: PCT/EP2006/060893

§ 371 (c)(1),
(2), (4) Date: Sep. 21, 2007

(87) PCT Pub. No.: WO2006/100229

PCT Pub. Date: Sep. 28, 2006

(65) Prior Publication Data

US 2008/0227990 A1    Sep. 18, 2008

(30) Foreign Application Priority Data

Mar. 22, 2005 (IT) .............................. MI05A0466

(51) Int. Cl.
*C07D 339/02* (2006.01)
(52) U.S. Cl. .......................................................... 549/39
(58) Field of Classification Search .................... 549/39
See application file for complete search history.

(56) References Cited

U.S. PATENT DOCUMENTS 6,462,202 B1    10/2002    Schuhbauer et al.

OTHER PUBLICATIONS

Christophe Crevisy et al., A New Iron-Mediated Strategy for the Synthesis of a-Lipoic Acid and Analogues; Eur. J. Org. Chem. 1998, pp. 1949-1954.
N.W. Fadnavis, et al., Lipase Catalyzed Regio- and Stereospecific Hydrolysis: Chemoenzymatic Synthesis of Both (R)- and (S)-enantiomers of a-Lipoic Acid; Tetrahedron: Asymmetry 9 (1998) pp. 4109-4112.
Preeti Dhar, et al., Piperidinium Tetrathiotungstate as Sulfur Transfer Reagant: Synthesis of Cyclic Disulfides; J. Org. Chem. 1992, 57, pp. 1699-1702.
Michael H. Brookes, et al., Synthesis of a-(R)- and a-(S)-Lipoic Acid from (S)-Malic Acid; J. Chem. Soc. Perkin Trans. 1 (1988) pp. 9-12.
Augusto Segre, et al., A New Synthesis of 6-Thioctic Acid (DL-a-Lipoic Acid); 6-Thioctic Acid, Jul. 5, 1957, pp. 3503-3505.
Edward Walton, et al., Synthesis of (+)-a-Lipoic Acid and Its Optical Antipode; JACS (1955) vol. 77, pp. 5144-5149.
D.S. Acker et al., Synthesis of Racemic, Optically Active and Radioactive a-Lipoic Acids; JACS (1957) pp. 6483-6487.

*Primary Examiner*—Taylor Victor Oh
(74) *Attorney, Agent, or Firm*—McCormick, Paulding & Huber LLP

(57) ABSTRACT

Process for purifying thioctic acid in water comprising the following steps: a) dissolving the thioctic acid in an aqueous alkaline solution or alternatively dissolving a thioctic acid salt, if necessary adjusting the pH to alkaline values, b) acidifying the solution from step (a) with an acid chosen from the class consisting of sulfuric acid, phosphoric acid, methanesulfonic acid to a pH between 5.4 and 5.8. c) isolating the thioctic acid precipitated in step (b) by conventional methods.

9 Claims, 4 Drawing Sheets

PROCESS FOR PURIFYING THIOCTIC ACID IN WATER

CROSS-REFERENCE TO RELATED APPLICATIONS

This application is entitled to the benefit of and incorporates by reference essential subject matter disclosed in International Application No. PCT/EP2006/060893 filed on Mar. 21, 2006 and Italian Patent Application No. MI2005A000466 filed on Mar. 22, 2005.

FIELD OF THE INVENTION

The present invention relates to a process for purifying thioctic acid in water.

BACKGROUND OF THE INVENTION

Thioctic acid is a substance found in nature, both in animal and plant cells, as the R enantiomer; it is a coenzyme for the oxidative decarboxylation of α-ketocarboxylic acids and an antioxidant able to regenerate vitamin C, vitamin E, glutathione and coenzyme Q10. Moreover, the raceme is employed for the treatment of hepatic disorders and neuropathies and in addition demonstrates cytoprotective anti-inflammatory and analgesic activity.

Syntheses of the racemic crude and optically active acid are conducted using methods described in Eur. J. 1998, 1949; Fadnavis et Al., Tetrahedron Asym., 1998, 9 4109, Dhar et Al., J. Org. Chem., 1992, 57, 1699, WO0230918, WO0230919.

The usual methods for purifying thioctic acid consist of recrystallization from solvents for example from n-pentane, cyclohexane, ethyl ether, ethyl acetate, etc. Thioctic acid is then recovered by filtration and centrifugation, and subsequently dried (J. Chem. Soc. Perkin Trans. 1 1988, 9, Segre et Al., J. Am. Chem. Soc., 1957, 3503; Walton et Al., J. Am. Chem. Soc., 1955, 77, 5144, Acker et Al., J. Am. Chem. Soc., 1954, 76, 6483).

The residual solvents present in the purification processes cannot be completely removed.

The active principles should not contain residual solvents in quantities exceeding safety levels.

To overcome this drawback a thioctic acid purification process was proposed in U.S. Pat. No. 6,462,202, conducted in the absence of organic solvents.

This process comprises in particular the following steps:
a) dissolving the thioctic acid in an aqueous alkaline solution or alternatively dissolving a salt thereof in water and suitably adjusting to an alkaline pH,
b) removing any solid impurities from the solution obtained in step (a),
c) acidifying the aqueous solution from step (a) or (b) to a pH between pH 1.0 and 5.0.
d) isolating the thioctic acid by known methods.

Even though this process presents considerable advantages, the thioctic acid purity was found not to be high because at the aforestated acid pHs, polymerization of the thioctic acid causes appreciable quantities of impurities to form, traceable by dissolving said product in chloroform.

A product with such characteristics does not comply with requirements that would allow its sale for the preparation of pharmaceutical formulations.

The need was therefore felt to provide a purification process for thioctic acid that would not present the inconveniences of the aforesaid process.

SUMMARY OF THE INVENTION

The Applicant has now surprisingly found a process for purifying thioctic acid in water that does not present the drawbacks of the aforesaid process for purifying thioctic acid in water.

The process of the present invention enables thioctic acid to be obtained in both the racemic form and in one of the two optically active forms: R(+) and S(−).

The process of the present invention comprises in particular the following steps:
a) dissolving the thioctic acid in an aqueous alkaline solution or alternatively dissolving a thioctic acid salt, if necessary adjusting the pH to alkaline values,
b) acidifying the solution from step (a) with an acid chosen from the class consisting of sulfuric acid, phosphoric acid, methanesulfonic acid to a pH between 5.4 and 5.8,
c) isolating the thioctic acid precipitated in step (b) by conventional methods.

DETAILED DESCRIPTION OF THE INVENTION

Figures 1, 2:
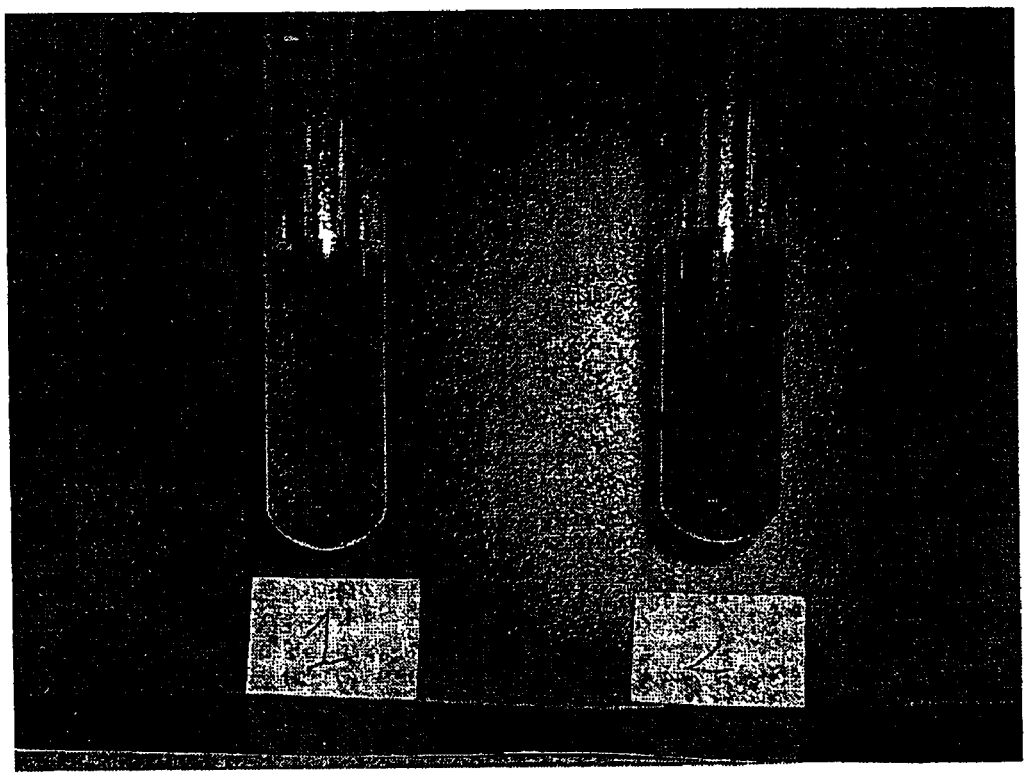
FIGS. 1-8 are photos that show the results of solubility tests of thioctic acid prepared as described in examples 1-8, respectively.
Figures 3, 4:
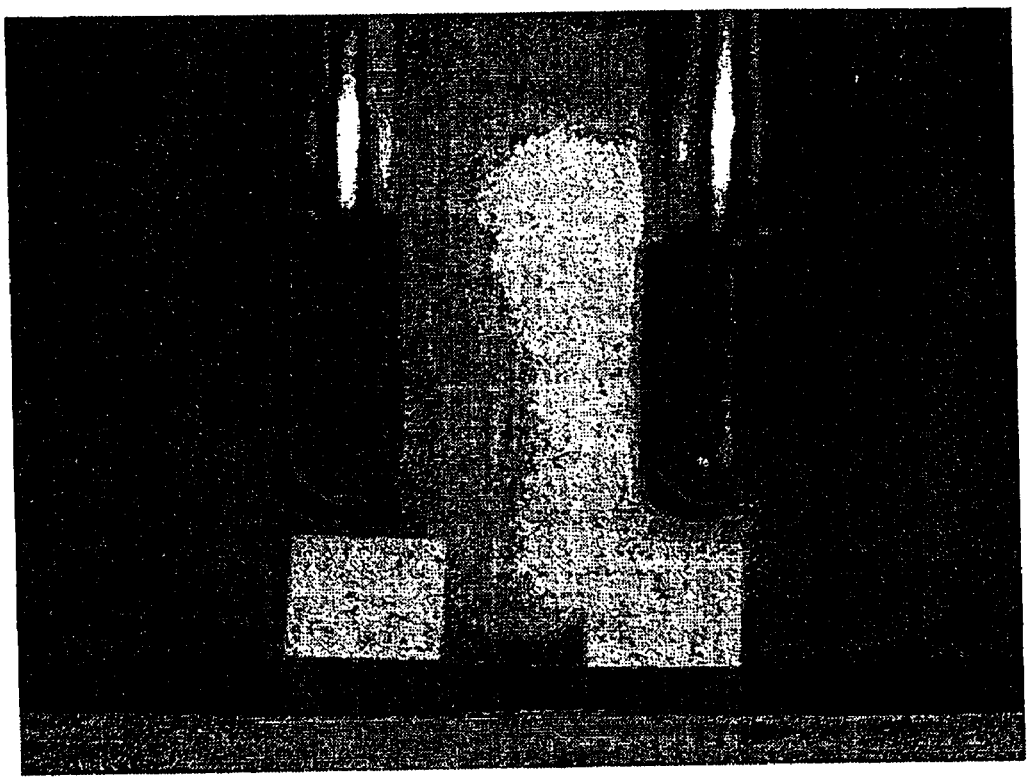
Figures 5, 6:
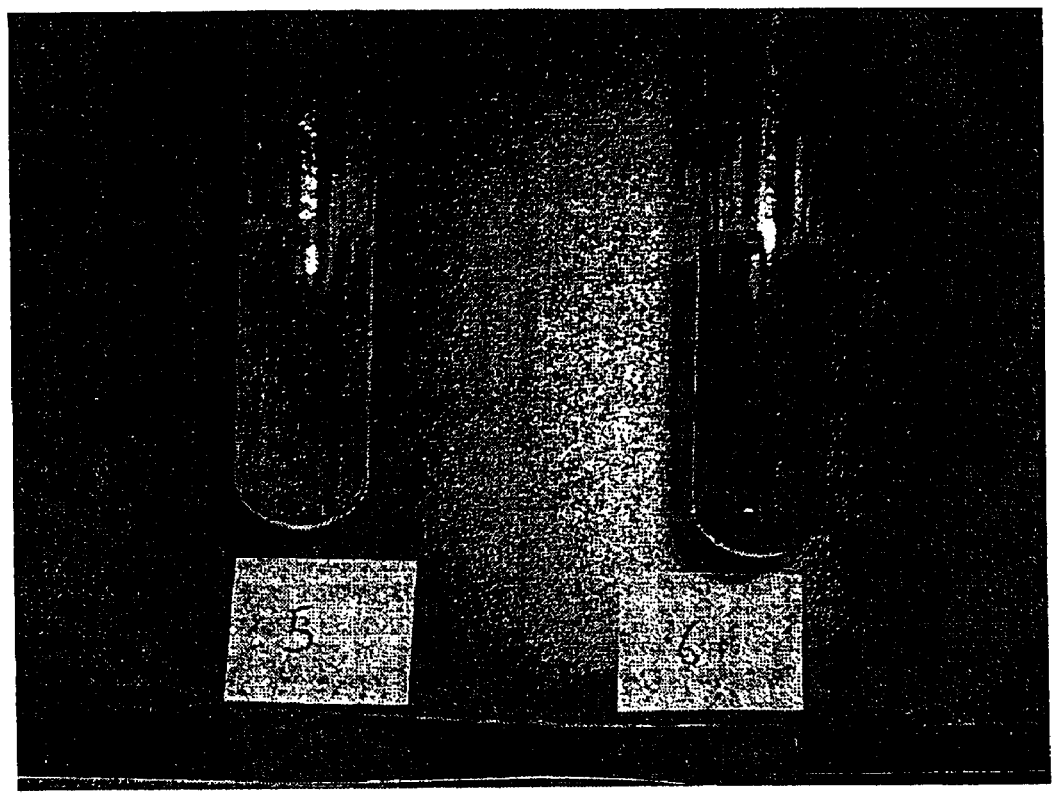
Figures 7, 8:
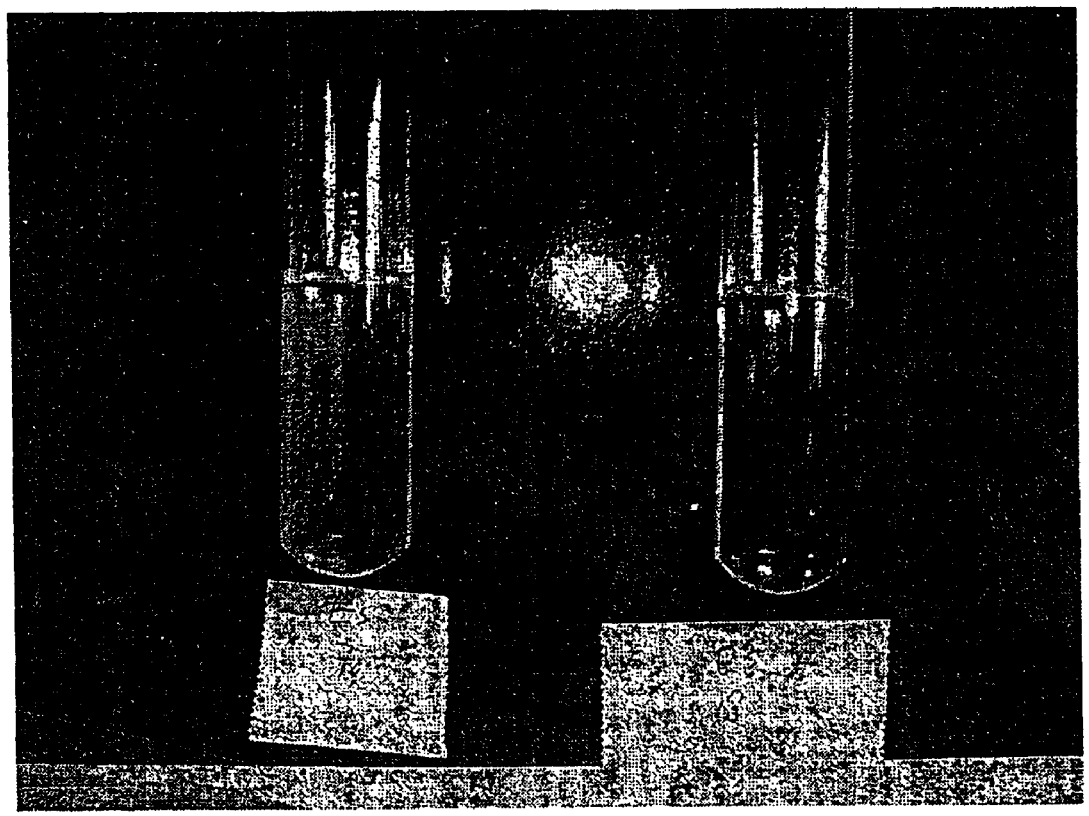

The Applicant has indeed found that if step (b) is not conducted using the aforesaid acids, but is conducted with hydrohalide acids such as hydrochloric and hydrobromic acids, even at pH 5.4-5.8, appreciable traces of the aforesaid polymer are inevitably formed.

Preferably step (b) of the process of the invention is conducted at a pH of between 5.5 and 5.7.

Preferably in step (b) the acid is added at a concentration between 5 and 10% by weight, more preferably at a concentration equal to 8% by weight.

The process of the present invention comprises a filtration step, subsequent to step (a), in which any impurities are removed.

Said filtration is preferably conducted under vacuum and achieved using a mechanical pump to remove any organic solvents present.

The Applicant has indeed found that only by filtering under vacuum, the solvent residue content can be further reduced to values lower than 5 ppm, while, vice versa, by operating a gravity filtration the quantity of solvents cannot be reduced to values less than 10 ppm.

Step (a) is preferably conducted at a pH between 8.5 and 14, even more preferably between 9 and 11, preferably employing a concentration of thioctic acid in water of between 0.1 and 5% by weight on the total weight of the composition. Some illustrative but non-limiting examples of the purification process of the present invention are given.

EXAMPLES

The thioctic acid used as the starting product in all the examples given hereinafter contains the following organic solvents:
cyclohexane: 524 ppm
ethyl acetate: 92 ppm toluene: 12 ppm Determination of the solvent residues in the products obtained from the examples was undertaken by means of headspace gas chromatography, dissolving the thioctic acid (about 250 mg) in dimethylformamide (5 ml) and water (5 ml).

Example 1

Repeat of Example 1 from the Degussa Patent 30 g (0.145 moles) of thioctic acid are suspended in 1000 ml of water at 20° C. 19.4 g of 30% aqueous sodium hydroxide (0.145 moles) are added drop-wise over a 1 hour period to obtain a solution at pH 9. The solution is filtered under vacuum through a paper filter and cooled to 0-3° C.

5% aqueous hydrochloric acid is added drop-wise over a 30 minute period until pH 1 is achieved, to obtain precipitation of the product.

The solid is filtered off and washed with water until the wash water is at neutral pH.

The wet product is dried at 30-35° C. for 18 hours to provide 27.9 g of solvent-free thioctic acid.

Test of solubility in chloroform (1 g in 10 ml of chloroform): cloudy solution with traces of polymer (undissolved lumps of various dimensions).

Example 2

Acidifying to pH 5.4 with HCl 30 g (0.145 moles) of thioctic acid are suspended in 1000 ml of water at 20° C. 20 g of 30% aqueous sodium hydroxide (0.15 moles) are added drop-wise over a 1 hour period to obtain a solution at pH 9. The solution is filtered under vacuum through a paper filter and cooled to 5° C.

5% aqueous hydrochloric acid is added drop-wise over a 30 minute period until pH 5.4 is achieved, to obtain precipitation of the product.

The solid is filtered off and washed with water until the wash water is at neutral pH.

The wet product is dried at 30-35° C. for 18 hours to provide 24.7 g of solvent-free thioctic acid.

Test of solubility in chloroform (1 g in 10 ml of chloroform): opalescent solution with traces of polymer (undissolved lumps of various dimensions).

Example 3

Acidifying to pH 2 with 5% $H_2SO_4$ 15 g (0.073 moles) of thioctic acid are suspended in 500 ml of water at 20° C. 10 g of 30% aqueous sodium hydroxide (0.073 moles) are added drop-wise over a 1 hour period to obtain a solution at pH 9. The solution is filtered under vacuum through a paper filter and cooled to 5° C.

5% aqueous sulfuric acid is added drop-wise over a 90 minute period until pH 2 is achieved, to obtain precipitation of the product.

The solid is filtered off and washed with water until the wash water is at neutral pH.

The wet product is dried at 30-35° C. for 18 hours to provide 13.5 g of solvent-free thioctic acid.

Test of solubility in chloroform (1 g in 10 ml of chloroform): opalescent solution with traces of polymer (undissolved lumps of various dimensions).

Example 4

Acidifying to pH 5.6 with 5% $H_2SO_4$ 15 g (0.073 moles) of thioctic acid are suspended in 500 ml of water at 20° C. 10 g of 30% aqueous sodium hydroxide (0.073 moles) are added drop-wise over a 1 hour period to obtain a solution at pH 9. The solution is filtered under vacuum through a paper filter and cooled to 5° C.

5% aqueous sulfuric acid is added drop-wise over a 90 minute period until pH 5.6 is achieved, to obtain precipitation of the product.

The solid is filtered off and washed with water until the wash water is at neutral pH.

The wet product is dried at 30-35° C. for 18 hours to provide 13.8 g of solvent-free thioctic acid.

Test of solubility in chloroform (1 g in 10 ml of chloroform): clear solution.

Example 5

Acidifying to pH 2 with 5% Methanesulfonic Acid 15 g (0.073 moles) of thioctic acid are suspended in 500 ml of water at 20° C. 10 g of 30% aqueous sodium hydroxide (0.073 moles) are added drop-wise over a 1 hour period to obtain a solution at pH 9. The solution is filtered under vacuum through a paper filter and cooled to 5° C.

5% aqueous methanesulfonic acid is added drop-wise over a 90 minute period until pH 2 is achieved, to obtain precipitation of the product.

The solid is filtered off and washed with water until the wash water is at neutral pH.

The wet product is dried at 30-35° C. for 18 hours to provide 13.7 g of solvent-free thioctic acid.

Test of solubility in chloroform (1 g in 10 ml of chloroform): cloudy solution with traces of polymer (in lumps).

Example 6

Acidifying to pH 5.6 with 5% Methanesulfonic Acid 15 g (0.073 moles) of thioctic acid are suspended in 500 ml of water at 20° C. 10 g of 30% aqueous sodium hydroxide (0.073 moles) are added drop-wise over a 1 hour period to obtain a solution at pH 9. The solution is filtered under vacuum through a paper filter and cooled to 5° C.

5% aqueous methanesulfonic acid is added drop-wise over a 90 minute period until pH 5.6 is achieved, to obtain precipitation of the product.

The solid is filtered off and washed with water until the wash water is at neutral pH.

The wet product is dried at 30-35° C. for 18 hours to provide 13.6 g of solvent-free thioctic acid.

Test of solubility in chloroform (1 g in 10 ml of chloroform): slightly opalescent solution without evidence of polymer.

Example 7

Acidifying to pH 2 with 8% $H_3PO_4$ 30 g (0.15 moles) of thioctic acid are suspended in 1000 ml of water at 20° C. 20 g of 30% aqueous sodium hydroxide (0.15 moles) are added drop-wise over a 1 hour period to obtain a solution at pH 9. The solution is filtered under vacuum through a paper filter and cooled to 5° C.

8% aqueous phosphoric acid is added drop-wise over a 90 minute period until pH 2 is achieved, to obtain precipitation of the product.

The solid is filtered off and washed with water until the wash water is at neutral pH.

The wet product is dried at 30-35° C. for 18 hours to provide 27.6 g of solvent-free thioctic acid.

Test of solubility in chloroform (1 g in 10 ml of chloroform): opalescent solution with traces of polymer.

Example 8

Acidifying to pH 5.5 with 8% $H_3PO_4$ 90 g (0.437 moles) of thioctic acid are suspended in 2900 ml of water at 10° C. 62 g of 30% aqueous sodium hydroxide (0.46 moles) are added drop-wise over a 1 hour period to obtain a solution at pH 9. The solution is filtered under vacuum through a paper filter and cooled to 5° C.

8% aqueous phosphoric acid is added drop-wise over a 90 minute period until pH 5.5 is achieved, to obtain precipitation of the product.

The solid is filtered off and washed with water until the wash water is at neutral pH.

The wet product is dried at 30-35° C. for 18 hours to provide 81 g of solvent-free thioctic acid.

Test of solubility in chloroform (1 g in 10 ml of chloroform): clear solution.
Melting point: 61-62° C.
K.F.=0.07%
Purity (HPLC): 99.9%
Solvents (cyclohexane, ethyl acetate, toluene): <5 ppm.

The invention claimed is:

1. Process for purifying thioctic acid comprising the following steps:
    a) dissolving the thioctic acid in an aqueous alkaline solution or alternatively dissolving a salt thereof and suitably adjusting to an alkaline pH,
    b) acidifying the solution derived from step (a) with an acid chosen from the class consisting of sulfuric acid, phosphoric acid, methanesulfonic acid to a pH between 5.4 and 5.8,
    c) isolating the thioctic acid precipitated in step (b) by filtration.

2. Process as claimed in claim 1, characterised in that step (b) is conducted at a pH between 5.5 and 5.7.

3. Process as claimed in claim 1, comprising a step subsequent to step (a) in which the alkaline solution from step (a) is filtered.

4. Process as claimed in claim 3, characterised in that said filtration is conducted under vacuum.

5. Process as claimed in claim 1, characterised in that step (a) is conducted at a pH between 8.5 and 15, employing a concentration of thioctic acid in water between 0.1 and 5% by weight on the total composition weight.

6. Process as claimed in claim 5, characterised in that said pH is between 9 and 11.

7. Process as claimed in claim 1, characterised in that in step (b) the acid is added at concentrations between 5 and 10% by weight.

8. Process as claimed in claim 7, characterised in that said concentration is equal to 8% by weight.

9. Process as claimed in claim 1 wherein thioctic acid is used in one of the two optically active forms: R(+) and S(−).

* * * * *